(12) United States Patent
Wang et al.

(10) Patent No.: US 11,009,432 B2
(45) Date of Patent: May 18, 2021

(54) PRETREATMENT DEVICE AND PRETREATMENT METHOD FOR FOOD SAFETY DETECTION

(71) Applicant: NUCTECH COMPANY LIMITED, Beijing (CN)

(72) Inventors: Hongqiu Wang, Beijing (CN); Zhuo Chen, Beijing (CN); Qianyu Zhou, Beijing (CN); Lichao Jiang, Beijing (CN); Shixin Zhang, Beijing (CN); Rui Fan, Beijing (CN)

(73) Assignee: NUCTECH COMPANY LIMITED, Beijing (CN)

(*) Notice: Subject to any disclaimer, the term of this patent is extended or adjusted under 35 U.S.C. 154(b) by 209 days.

(21) Appl. No.: 16/235,863

(22) Filed: Dec. 28, 2018

(65) Prior Publication Data

US 2019/0204190 A1 Jul. 4, 2019

(30) Foreign Application Priority Data

Dec. 29, 2017 (CN) .......................... 201711485199.1

(51) Int. Cl.
| | |
|---|---|
| *B01F 11/00* | (2006.01) |
| *G01N 1/28* | (2006.01) |
| *G01N 1/34* | (2006.01) |
| *G01N 1/38* | (2006.01) |
| *G01N 33/02* | (2006.01) |
| *G01N 1/40* | (2006.01) |
| *G01N 35/00* | (2006.01) |

(52) U.S. Cl.
CPC .......... *G01N 1/286* (2013.01); *B01F 11/0008* (2013.01); *B01F 11/0014* (2013.01);
(Continued)

(58) Field of Classification Search
CPC ... B01F 11/00; B01F 11/0008; B01F 11/0014; G01N 1/00; G01N 1/18; G01N 1/28;
(Continued)

(56) References Cited

U.S. PATENT DOCUMENTS

| | | | | |
|---|---|---|---|---|
| 2,560,107 A | * | 7/1951 | Hewson | G01N 35/025 422/64 |
| 4,004,883 A | * | 1/1977 | Meyer | B01F 11/0014 422/566 |

(Continued)

FOREIGN PATENT DOCUMENTS

| | | |
|---|---|---|
| GB | 2 124 102 A | 2/1984 |
| WO | WO 01/24904 A1 | 4/2001 |

*Primary Examiner* — Nguyen Q. Ha
(74) *Attorney, Agent, or Firm* — Christensen, Fonder, Dardi & Herbert PLLC

(57) ABSTRACT

A pretreatment device for food safety detection, including: a base; a vortex oscillator disposed on the base; and a container holding mechanism disposed on the base and configured to hold a container such that the container is positioned above the vortex oscillator, wherein the vortex oscillator is configured to cooperate with the container holding mechanism to treat materials contained in the container. The present disclosure further provides a pretreatment method for food safety detection. By means of the pretreatment device and the pretreatment method according to the present disclosure, it can perform pretreatment work of food safety detection efficiently and simply, and save labor costs.

16 Claims, 5 Drawing Sheets

(52) U.S. Cl.
CPC .................. *G01N 1/34* (2013.01); *G01N 1/40* (2013.01); *G01N 1/405* (2013.01); *G01N 33/02* (2013.01); *G01N 2001/2866* (2013.01); *G01N 2001/4027* (2013.01); *G01N 2035/00524* (2013.01)

(58) Field of Classification Search
CPC ............ G01N 1/286; G01N 1/34; G01N 1/38; G01N 1/40; G01N 1/405; G01N 33/02; G01N 2001/2866; G01N 2001/4027; G01N 2035/00524

See application file for complete search history.

(56) References Cited

U.S. PATENT DOCUMENTS

| | | |
|---|---|---|
| 5,195,825 A | 3/1993 | Ringrose |
| 5,496,741 A | 3/1996 | Pawliszyn |
| 6,573,088 B2 * | 6/2003 | Gemmell ............ G01N 35/0092 422/64 |
| 8,008,066 B2 * | 8/2011 | Lair ...................... C12Q 1/6813 435/287.3 |
| 9,695,392 B2 * | 7/2017 | Sherman ................ C12M 27/16 |
| 2007/0125186 A1 * | 6/2007 | Ruser .................. B01F 11/0014 366/111 |
| 2008/0124251 A1 * | 5/2008 | Chen ........................ G01N 1/40 422/400 |
| 2010/0126286 A1 * | 5/2010 | Self ...................... G01N 35/026 73/863.81 |
| 2011/0096620 A1 * | 4/2011 | Kotler ................. B01F 11/0008 366/208 |
| 2012/0107197 A1 * | 5/2012 | Luethi ................. B01F 11/0028 422/561 |
| 2012/0182829 A1 * | 7/2012 | Beumer .............. B01F 11/0014 366/218 |
| 2018/0200732 A1 * | 7/2018 | Zhang ....................... B04B 9/08 |

* cited by examiner

PRETREATMENT DEVICE AND PRETREATMENT METHOD FOR FOOD SAFETY DETECTION

CROSS-REFERENCE TO RELATED APPLICATION

This application claims priority of Chinese Patent Application No. 201711485199.1 filed on Dec. 29, 2017 in the State Intellectual Property Office of China, the disclosure of which is incorporated herein by reference in entirety.

TECHNICAL FIELD

Embodiments of the present disclosure relate to the field of food safety and detection technology, and in particular, to a pretreatment device for food safety detection and a pretreatment method for food safety detection.

BACKGROUND

Food safety is closely related to the body health and life safety of the public and increasingly concerned. In order to ensure the safety of food, it is necessary to properly detect and monitor the food at nodes of food supply chain, so as to obtain information about ingredients and harmful substances of the food by the detection. A number of food safety detection techniques have been proposed out in the exiting techniques, for example, detecting additive levels or pesticide residues in the food.

For the safe detection of food, it is generally necessary to pre-treat or pretreat the food or foodstuff to facilitate the implementation of the detection. For example, common pretreatments include pulverizing and pulping the food, adding a solvent to dissolve a target substance (for example, additive component) to be detected in the solvent, and so on. At present, a pretreatment of food safety detection is often implemented manually, without any dedicated automatic pretreatment devices.

The pretreatment procedure of food safety detection implemented manually has the following disadvantages: 1) it involves in complicated operation steps, and then results in operators are required to operate one step by one step according to predetermined pretreatment steps with the aid of an operation manual, thus, the processing speed is slow and it requires the operator to have certain capabilities about pretreatment; 2) it requires a lot of manpower, and due to different operating habits for different operators, it is difficult to standardize the entire pretreatment processes, thereby it readily introduces experimental system errors caused by the different operating habits; 3) it has high cost, and it is difficult to accurately control experimental consumables, storage of reagents, and use of solid powder samples or the like.

SUMMARY

The present disclosure intends to at least partially overcome the problems or deficiencies in the prior art, and to provide a pretreatment device for food safety detection that is capable of performing pretreatment work of food safety detection efficiently and simply.

The present disclosure also intends to provide a pretreatment device for food safety detection to save labor costs.

The present disclosure further intends to provide a pretreatment device for food safety detection that reduces reliance on the operator's experience, avoids effects of human factors, and improves accuracy of food safety detection.

The present disclosure still intends to provide a pretreatment method for food safety detection.

In order to achieve at least one of the above objects, the technical solutions of the present disclosure are as follows:

A pretreatment device for food safety detection, comprising:
a base;
a vortex oscillator disposed on the base; and
a container holding mechanism disposed on the base and configured to hold a container such that the container is positioned above the vortex oscillator, wherein the vortex oscillator is configured to cooperate with the container holding mechanism to treat materials contained in the container.

According to a preferred embodiment of the present disclosure, the pretreatment device further comprises a mobile apparatus and a feeding mechanism, a drying mechanism, a first pumping mechanism and a second pumping mechanism that are disposed on the mobile apparatus, wherein the feeding mechanism, the drying mechanism, the first pumping mechanism and the second pumping mechanism are capable of moving to and above the container under driving of the mobile apparatus, wherein the first pumping mechanism is configured to pump a first solvent into the container;
wherein the feeding mechanism is configured to supply an extraction salt into the container;
wherein the drying mechanism is configured to dry a liquid in the container; and
wherein the second pumping mechanism is configured to pump a second solvent into the container.

According to a preferred embodiment of the present disclosure, at least one of the first pumping mechanism and the second pumping mechanism is provided with a platen, which is configured to press against a top of the container to initiate a vortex oscillation of the container.

According to a preferred embodiment of the present disclosure, the mobile apparatus comprises a translation mechanism, a slewing mechanism and/or a lifting mechanism.

According to a preferred embodiment of the present disclosure, the container holding mechanism comprises a support frame, a supporting arm extending from the support frame and a clamping head disposed on an end of the supporting arm away from the support frame, and wherein the clamping head is configured to clamp the container.

According to a preferred embodiment of the present disclosure, the lifting mechanism comprises a moving block, a stand and a rod, the rod extends in a vertical direction and is fixed to the stand, the moving block is configured to be movable on the rod, and the feeding mechanism, the drying mechanism, the first pumping mechanism and/or the second pumping mechanism is/are fixedly mounted to the moving block.

According to a preferred embodiment of the present disclosure, the moving block is configured to have a hexahedral profile, wherein the feeding mechanism, the first pumping mechanism and the second pumping mechanism are respectively fixed to three surfaces of the moving block parallel to an extending direction of the rod, and the drying mechanism is fixed to the stand.

According to a preferred embodiment of the present disclosure, the feeding mechanism comprises a hopper, a dispenser and a feeding mechanism hanger, wherein the hopper is configured for containing the extraction salt, the dispenser is arranged at an outlet of the hopper for dispensing the extraction salt.

According to a preferred embodiment of the present disclosure, the drying mechanism comprises a fan, an air collecting cylinder, a blowing port, and a drying mechanism hanger.

According to another aspect of the present disclosure, there is provided a pretreatment method for food safety detection, using the pretreatment device for food safety detection according to any one of the above embodiments.

By means of the pretreatment device and the pretreatment method according to the present disclosure, the pretreatment work of food safety detection can be performed simply and efficiently. The present disclosure can save manpower, without requiring professional operators to carry out the complicated pretreatment work of food safety detection, and any untrained person can automatically finish the pretreatment work through this device. The pretreatment device for food safety detection according to the present disclosure is simple and safe to operate, without requiring the operators to touch any chemical liquid reagent and inorganic salt compound, thereby reducing environmental pollution. In addition, the pretreatment work for food safety detection according to the present disclosure can save a lot of time, because the device automatically performs addition of reagent and salt solid, blow-drying, oscillation and the like.

DETAILED DESCRIPTION OF EMBODIMENTS

Figure 1:
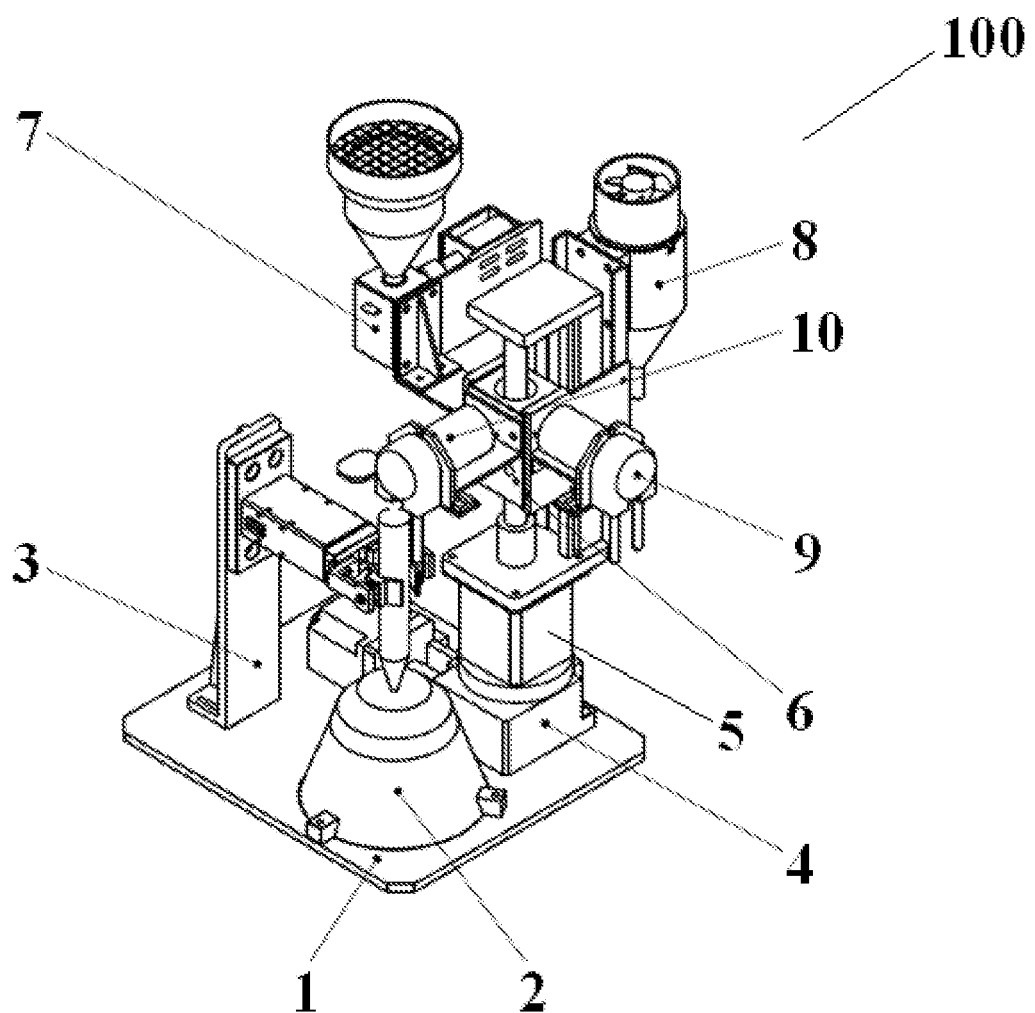
FIG. 1 is a general schematic view of a pretreatment device for food safety detection according to an embodiment of the present disclosure.

The present disclosure will be further described below with reference to the accompanying drawings and the exemplary embodiments, wherein the same or similar reference numerals refer to the same or similar component. In addition, numerous details are explained for interpretation in the following description, so as to provide a full understanding to the embodiments of the present disclosure. However, it is apparent that one or more embodiments can be implemented without these specific details. In other instances, known structures and devices are illustrated in the drawings in a simplified manner.

According to a general concept of the present disclosure, there is provided a pretreatment device for food safety detection, comprising: a base; a vortex oscillator disposed on the base; and a container holding mechanism disposed on the base and configured to hold a container such that the container is positioned above the vortex oscillator, wherein the vortex oscillator is configured to cooperate with the container holding mechanism to treat materials contained in the container. FIG. 1 is a general schematic view of a pretreatment device for food safety detection according to an embodiment of the present disclosure. As shown in FIG. 1, a pretreatment device 100 for food safety detection includes a base 1, a vortex oscillator 2, a container holding mechanism 3, a translation mechanism 4, a slewing mechanism 5, a lifting mechanism 6, a feeding mechanism 7, a drying mechanism 8, a first pumping mechanism 9, and a second pumping mechanism 10.

Figure 3:
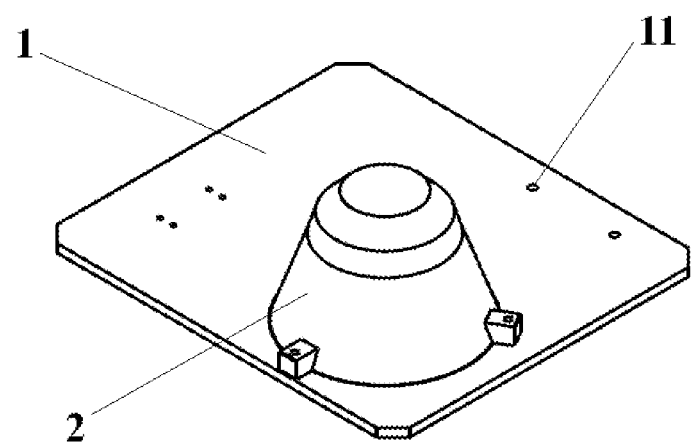
FIG. 3 is a schematic view of a base and a vortex oscillator according to an embodiment of the present disclosure.

In the embodiment shown in FIG. 1, the base 1 is a flat square substrate. Referring to FIG. 3, it is made of a metal material, and it can be placed on a table or desk and fixed by a fixing device. Alternatively, the base 1 can be constructed to be a solid or hollow block, preferably the base 1 is relatively heavy in order to lower a gravity center of the entire pretreatment device so that it may be securely positioned on the table or desk. As shown in FIG. 3, a plurality of mounting holes 11 may be formed in the base 1 for attaching and fixing the container holding mechanism 3, the translation mechanism 4, and the like to the base 1 for example by bolts. Exemplarily, the container holding mechanism 3 is fixed by four mounting holes 11, and the translation mechanism 4 is fixed by two mounting holes 11. The vortex oscillator 2 may be of known vortex oscillator in the prior art, in the shape of a substantially frustum, fixed at a corner of the base 1. The container holding mechanism 3 is fixed at another corner of the base 1 adjacent to the corner where the vortex oscillator 2 is located, thereby a line connecting a center of the container holding mechanism 3 and a center of the vortex oscillator 2 is substantially parallel to a side of the base 1, the translation mechanism 4 and other components carried thereon are arranged on the base 1 substantially in parallel with a column formed by the container holding mechanism 3 and the vortex oscillator 2. In this way, the entire pretreatment device 100 has a relatively uniform distribution of weight on the base 1, facilitating stable placement of the pretreatment device 100 and stabilization of the pretreatment device 100 when the vortex oscillator 2 is in operation. Preferably, the arrangement of the vortex oscillator 2 on the base 1 may be fixed by means of three bolts evenly distributed along a circumference of the vortex oscillator 2.

Figure 4:
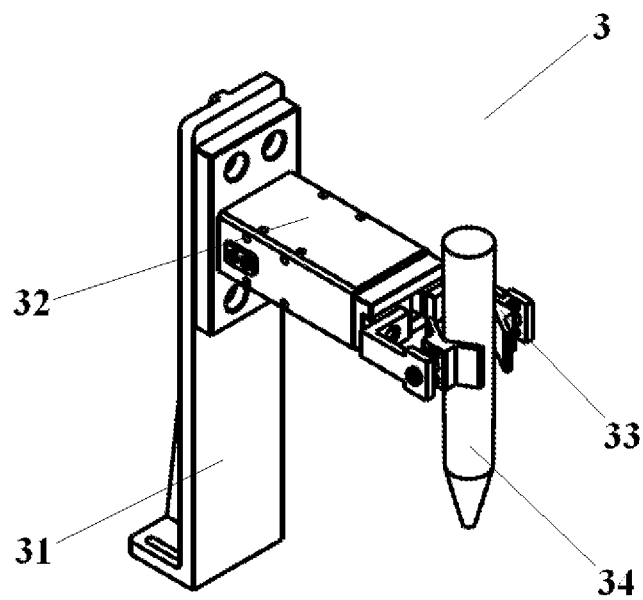
FIG. 4 is a schematic view of a container holding mechanism according to an embodiment of the present disclosure.

The container holding mechanism 3 includes a support frame 31, a supporting arm 32 extending from the support frame 31, and a clamping head 33 disposed on an end of the supporting arm 32 away from the support frame 31. Referring to FIG. 4, the clamping head 33 is configured to clamp a container 34 so that the container 34 is positioned above the vortex oscillator 2, wherein the container holding mechanism 3 can cooperate with the vortex oscillator 2 to treat materials contained in the container 34. In an example of performing food safety detection, the container 34 contains a sample of the food to be treated, and herein the container 34 is a centrifuge tube. Specifically, the support frame 31 is of L shape, including a horizontal plate and a vertical plate, and the horizontal plate is provided with a linear groove for cooperating with the mounting holes on the base 1 to fix the container holding mechanism 3 by bolts, the design of the linear groove allows the support frame 31 to be adjusted relative to the vortex oscillator 2 (release the bolts and then move the support frame 31) to change the distance between the container holding mechanism and the vortex oscillator. In this way, the container holding mechanism 3 may be adapted to a plurality of containers of different types and shapes so that they can all be positioned right above the center of the vortex oscillator 2. Reinforcing ribs may be provided on a back side of the vertical plate to enhance strength of the container holding mechanism 3. The supporting arm 32 extends horizontally, and it may be fixed to the support frame 31 by a connecting device or integrally formed with the support frame 31. The clamping head 33 is mounted at one end of the supporting arm 32, and the clamping head 33 may apply an elastic preload force to the container 34, so as to clamp the container 34. Furthermore, there is a moving gap for the clamping head 33 to move relative to the supporting arm 32, to accommodate amount of vibration of the clamping head 33 when the container 34 vibrates.

Preferably, the supporting arm 32 is constructed of a retractable sleeve, and the supporting arm 32 further includes a snap unit and a scale line, for locking amount of extension of the sleeve after the sleeve has been telescoped to a desired length, and metering the amount of extension of the sleeve.

Figure 2:
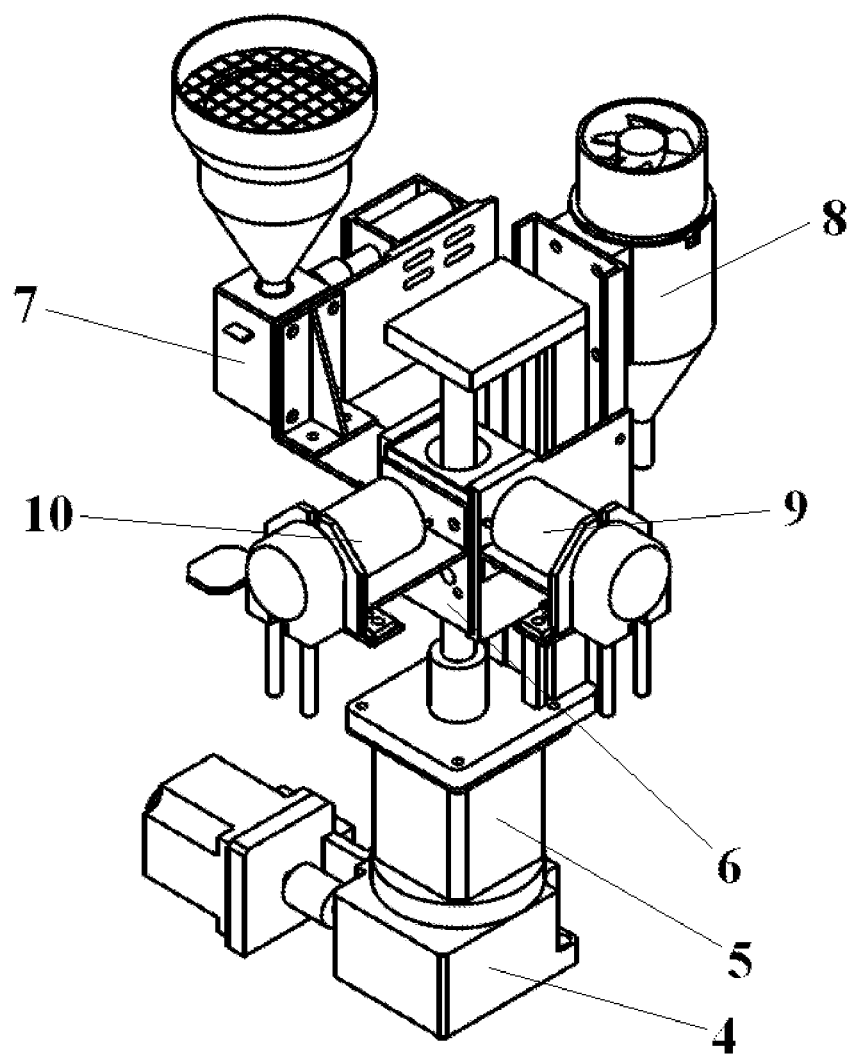
FIG. 2 illustrates components carried by a mobile apparatus according to an embodiment of the present disclosure.

FIG. 2 illustrates components carried by a mobile apparatus according to an embodiment of the present disclosure. As shown in FIG. 2, the translation mechanism 4, the slewing mechanism 5 and the lifting mechanism 6 constitute the mobile apparatus of the present disclosure, and they will be described in detail below. The feeding mechanism 7, the drying mechanism 8, the first pumping mechanism 9, and the second pumping mechanism 10 are disposed on the mobile apparatus, and the feeding mechanism 7, the drying mechanism 8, the first pumping mechanism 9, and the second pumping mechanism 10 are capable of moving to and above the container 34 under the driving of the mobile apparatus. The first pumping mechanism 9 is configured to pump a first solvent, for example an organic solvent, into the container 34; the feeding mechanism 7 is configured to supply an extraction salt into the container 34; the drying mechanism 8 is configured to dry a liquid in the container 34; and the second pumping mechanism 10 is configured to pump a second solvent, for example water, into the container 34.

Figure 7:
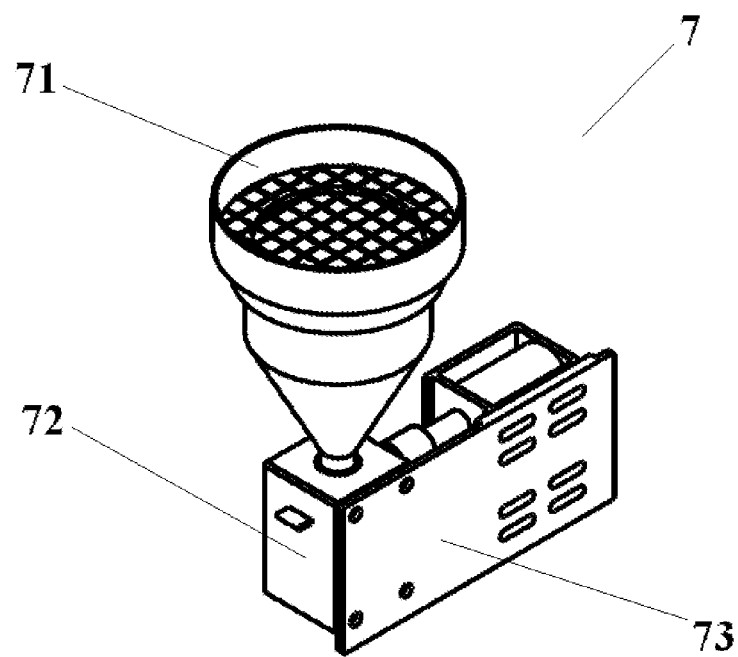
FIG. 7 is a schematic view of a feeding mechanism according to an embodiment of the present disclosure.
Figure 8:
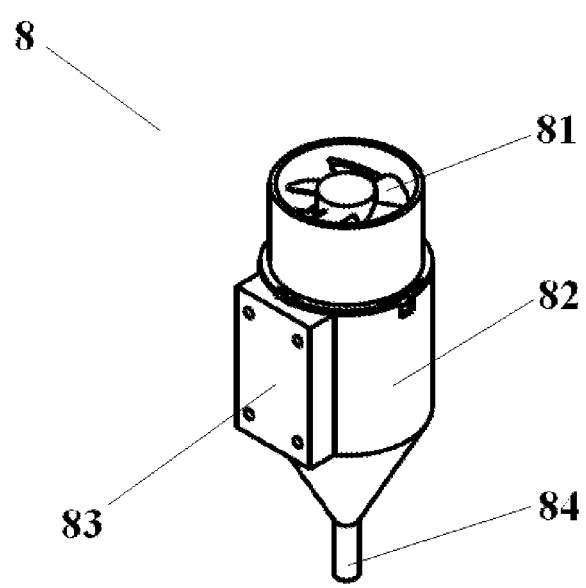
FIG. 8 is a schematic view of a drying mechanism according to an embodiment of the present disclosure.

The feeding mechanism 7 includes a hopper 71, a dispenser 72 and a feeding mechanism hanger 73, as shown in FIG. 7, the hopper 71 is configured for containing the extraction salt, and the dispenser 72 is arranged at an outlet of the hopper 71 for dispensing the extraction salt. The hopper 71 has a substantially inverted conical shape, and includes a plurality of honeycomb-shaped spaces inside the hopper 71. For example, the plurality of said spaces are formed by the intersection of partition plates. The design of the plurality of honeycomb-shaped spaces may avoid the bonding of the extraction salt. The dispenser 72 may quantitatively dispense the extraction salt in the hopper 71, and the dispenser is connected to the feeding mechanism hanger 73, which is fixedly connected to a moving block 61 which will be described later.

The drying mechanism 8 includes a fan 81, an air collecting cylinder 82, a blowing port 84, and a drying mechanism hanger 83. The fan 81 is disposed above the air collecting cylinder 82, the blowing port 84 is disposed below the air collecting cylinder 82, and a tapering conical design is adopted in a portion between the air collecting cylinder 82 and the blowing port 84, so that the blowing port 84 has a quite smaller cross-sectional area than that of the air collecting cylinder 82. In this way, the wind blown from the fan 81 is pressurized and accelerated at the blowing port 84, which is advantageous for quickly drying the liquid to be treated. The air collecting cylinder 82 is connected to the drying mechanism hanger 83, and the drying mechanism hanger 83 is fixedly connected to a stand 62 which will be described later.

The first pumping mechanism 9 and the second pumping mechanism 10 may pump the liquid pneumatically, hydraulically or electro-dynamically, and they are also fixedly mounted to the moving block 61, wherein the first solvent pumped by the first pumping mechanism 9 is different from the second solvent pumped by the second pumping mechanism 10, thereby allowing the pretreatment device according to the present disclosure to have different solvent options.

Advantageously, the first pumping mechanism 9 and/or the second pumping mechanism 10 are provided with a platen, for example the platen is arranged on the second pumping mechanism 10 (referring to FIG. 2). The platen may press against the top of the container 34, to initiate vortex oscillation of the container 34. The platen is a common component in a vortex oscillation device, and the pretreatment device 100 for food safety detection according to the present disclosure is made more compact by arranging the platen on the first pumping mechanism 9 and/or the second pumping mechanism 10. Moreover, it is possible to perform vortex oscillation process quickly after pumping the solvent into the container 34, since the vortex oscillator may be initiated only by slightly rotating and moving the first pumping mechanism 9 and/or the second pumping mechanism 10.

Figure 5:
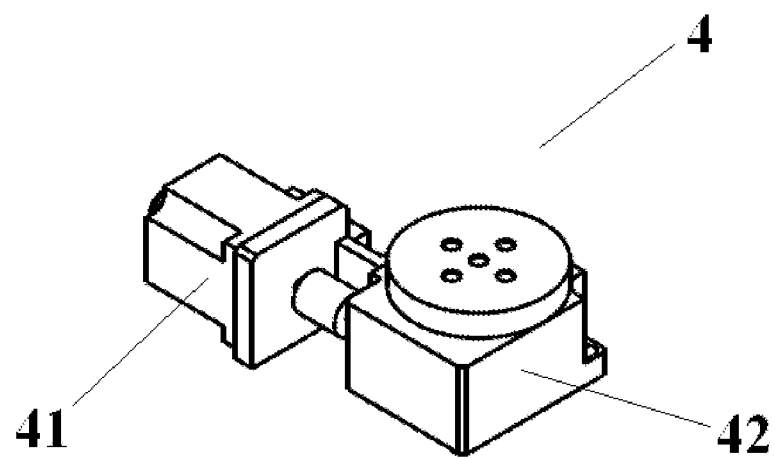
FIG. 5 is a schematic view of a translation mechanism according to an embodiment of the present disclosure.
Figure 6:
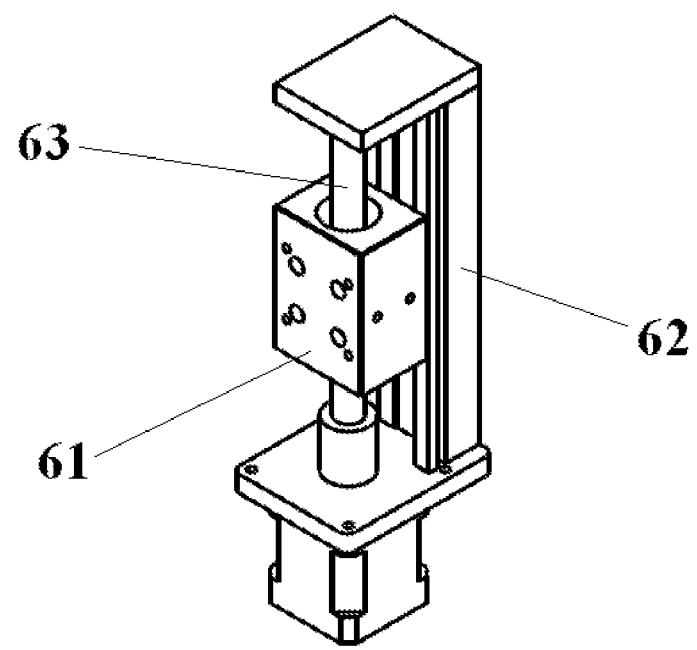
FIG. 6 is a schematic view of a lifting mechanism according to an embodiment of the present disclosure.

FIG. 5 is a schematic view of a translation mechanism according to an embodiment of the present disclosure; and FIG. 6 is a schematic view of a lifting mechanism according to an embodiment of the present disclosure. Referring to FIGS. 1, 2, 5, 6, the translation mechanism 4 is fixedly mounted to the base 1, and includes a motor 41 and a support table 42. The motor 41 drives the support table 42 to move in a straight line by a transmission mechanism. The slewing mechanism 5 enables to pivot around an axis. The lifting mechanism 6 includes a moving block 61, a stand 62 and a rod 63. The stand 62 has a U shape, the rod 63 extends in a vertical direction and is fixed to the stand 62, and the moving block 61 is configured to be movable on the rod 63. The feeding mechanism 7, the drying mechanism 8, the first pumping mechanism 9, and/or the second pumping mechanism 10 may be fixedly mounted to the moving block 61. In the embodiment shown in FIG. 2, the moving block 61 is configured to have a hexahedral profile, wherein the feeding mechanism 7, the first pumping mechanism 9 and the second pumping mechanism 10 are respectively fixed to three surfaces of the moving block 61 parallel to an extending direction of the rod 63, and the drying mechanism 8 is fixed to the stand 62. With such an arrangement, the above four operating members may be respectively disposed on the four surfaces surrounding the center of the moving block, thereby obtaining a compact structure. Since it is not critical to precisely position the drying mechanism 8 in the vertical direction, the drying mechanism 8 may be disposed on the stand 62. In this way, the drying mechanism 8 can achieve horizontal and circumferential positioning, but cannot be adjusted in the vertical direction.

It can be seen from the above that the pretreatment device for food safety detection according to the present disclosure is generally divided into three parts, a load bearing portion, an operating portion and a holding portion. The load bearing part is composed of the base and the vortex oscillator, the base is responsible for the stable support of the whole device and the fixing of various parts. Food sample to be treated in an experiment is placed on the vortex oscillator, and specifically the food sample is placed in a vertical centrifuge tube. The operating mechanism has a total of seven parts, specifically, the translation mechanism 4, the slewing mechanism 5, the lifting mechanism 6, the feeding mechanism 7, the drying mechanism 8, the first pumping mechanism 9, and the second pumping mechanism 10. The translation mechanism 4 is responsible for the positioning of each of sub-operating mechanisms in the operating mechanism in a horizontal direction, the slewing mechanism 5 is responsible for the positioning of each of sub-operating mechanisms in the operating mechanism in a circumferential direction, and the lifting mechanism 6 is responsible for the positioning of each of sub-operating mechanisms in the operating mechanism in a vertical direction. The feeding mechanism (for example, a salt feeding mechanism) 7 may include a storage tank for storing a salt compound and a motor-controlled electromagnet switch, in which the electromagnet switch is responsible for realizing the dispensing of the salt compound in the storage tank, and the salt compound falls into the centrifuge tube due to gravity thereof. The drying mechanism is responsible for evaporating the liquid in the centrifuge tube by blowing hot air; the first pumping mechanism 9 and the second pumping mechanism 10 are responsible for pumping the liquids in reagent bottles into the centrifuge tube, respectively. The holding portion is mainly composed of a support frame and a robot arm, the support frame is responsible for connecting the base with the holding portion, and the robot arm is responsible for clamping and fixing the centrifuge tube placed in the vortex oscillator.

The pretreatment device for food safety detection according to the present disclosure has been described above with reference to FIGS. 1-8, and next, its operating process will be described below in conjunction with a rapid sample pretreatment technique for agricultural product detection. The pretreatment is the longest and most labor-intensive part of food detection, and the quality of the pretreatment determines the accuracy and precision of the analysis.

The specific pretreatment method is similar to high performance liquid chromatography and solid phase extraction, both of which utilize the interaction of adsorbent filler with impurities in the substance, wherein the adsorbent filler adsorbs the impurities, thereby achieving the purpose of removing impurity. Specifically, after the homogenized sample is extracted by acetonitrile, it is separated and layered by extraction salt, and then by the principle of dispersion and extraction of the substance, PSA or other adsorbent is used to be combined with most of the interfering substances in the substance, and then they are removed by a centrifugation method, thereby achieving the purpose of purification. The pretreatment method is fast, simple, inexpensive, effective, reliable, and safe. The operating process using the pretreatment device for food safety detection is as follows:

the food sample that needs to be pretreated is mashed and homogenized, then placed in a centrifuge tube, and then the centrifuge tube together with the food sample is placed on a vortex oscillator 2, and the motor is controlled to clamp the clamping head 33 to fix the position of the centrifuge tube;

by controlling the translation mechanism 4, the slewing mechanism 5 and the lifting mechanism 6, the first pumping mechanism 9 is located directly above the centrifuge tube, and the motor for the first pumping mechanism 9 is controlled to pump the first solvent into the centrifuge tube;

by controlling the translation mechanism 4, the slewing mechanism 5 and the lifting mechanism 6, the feeding mechanism 7 is located directly above the centrifuge tube, and the electromagnet switch of the feeding mechanism 7 is controlled to allow the salt compound in the hopper 71 to fall into the centrifuge tube, and then the platen on the second pumping mechanism 10 is controlled to press against the top of the centrifuge tube, so that the centrifugal tube is subjected to a vortex oscillation treatment;

after the liquid is kept still for a while, the supernatant is sucked into another purification centrifuge tube, and the platen on the second pumping mechanism 10 is controlled to press against the top of the centrifuge tube, so that the centrifuge tube starts a stable vortex oscillation under the action of the vortex oscillator 2;

after the liquid is kept still for a while, the supernatant is sucked into another empty centrifuge tube, then the centrifuge tube is placed on the vortex oscillator 2 and clamped by the clamping head 33, and the translation mechanism 4, the slewing mechanism 5 and the lifting mechanism 6 are controlled in such a way that the drying mechanism 8 is located directly above the centrifuge tube to volatilize and dry the liquid in the centrifuge tube;

by controlling the translation mechanism 4, the slewing mechanism 5, and the lifting mechanism 6, the second pumping mechanism 10 is located directly above the centrifuge tube, and the motor for the second pumping mechanism 10 is controlled to pump the second solvent into the centrifuge tube.

In another aspect, there is provided in the present disclosure a pretreatment method for food safety detection, using the pretreatment device 100 for food safety detection according to any one of the foregoing embodiments.

In summary, the pretreatment method for food safety detection according to the present disclosure includes (taking the detection of pesticide residues as an example): 1) homogenizing: pulverizing the food to be detected, and smashing the pulverized powder into juice; 2) extracting pesticide: adding an organic solvent to the container containing the above-described juice to dissolve the pesticide component in the organic solvent; 3) purifying and removing impurities: taking out the organic solvent in which the pesticide component is dissolved and placing it in another container, and adding extraction salt into this container to purify or remove the impurities in the solution; 4) replacing with water solvent (drying+solvent re-dissolving): placing the above-described purified solution in still another container and performing a drying treatment to it, drying of the organic solvent, then adding water to this container, thereby completing the pretreatment work and obtaining a sample prepared for food safety detection.

By means of the pretreatment device and the pretreatment method according to the present disclosure, the pretreatment work of food safety detection can be performed simply and efficiently. The present disclosure can save manpower, without requiring professional operators to carry out the complicated pretreatment work of food safety detection, and any untrained person can automatically finish the pretreatment work through this device. The pretreatment device for food safety detection according to the present disclosure is simple and safe to operate, without requiring the operators to touch any chemical liquid reagent and inorganic salt compound, thereby reducing environmental pollution. In addition, the pretreatment work for food safety detection according to the present disclosure can save a lot of time, because the device automatically performs addition of reagent and salt solid, blow-drying, oscillation and the like.

In summary, the present disclosure utilizes a slewing platform or the like to effectively combine the processes such as the addition of reagent, salt powder compound, the blow-drying and oscillation, and the like, which are required in a food safety pretreatment process, into one device, and the device is simple and convenient to use. Moreover, the present disclosure utilizes a control system to standardize and program the food safety pretreatment process, saving manpower and automating the entire process.

Further, the pretreatment device for food safety detection according to the present disclosure may further comprise a heating device, which may be constructed as an electric heating sleeve, the electric heating sleeve may be coated around the outer circumference of the container or the centrifuge tube, to heat the materials inside the container. The electric heating sleeve may be used to increase the temperature of the solvent in the container, to accelerate the processes of extracting and purifying and removing impurities.

In addition, pairs of perforations may be provided in the base, and the pretreatment device may further include a fixing strap that is configured to pass through the perforations to bind the base of the pretreatment device to other fixing members, to enhance the stability of the entire device when the vortex oscillator is operating. Further, the pretreatment device further includes a mask for covering the pretreatment device, thereby preventing ash from being fallen in the hopper or the like when the pretreatment device is not in operation. In order to improve the integration of the pretreatment device, the slewing mechanism is configured to have a hexahedral profile, one or more reagent kits and one or more container holders may be provided on the four vertical surfaces of the slewing mechanism, the kits are configured to accommodate the substances for example solvent or extraction salt, and the container holders are configured to hold the containers.

While some exemplary embodiments of the present disclosure have been given in the above description, it will be understood by those skilled in the art that modifications may be made to these exemplary embodiments without departing from the principle and spirit of the present disclosure, and the scope of the present disclosure is defined by the claims and their equivalents.

LIST OF REFERENCE NUMERALS 100 pretreatment device
1 base
2 vortex oscillator
3 container holding mechanism
4 translation mechanism
5 slewing mechanism
6 lifting mechanism
7 feeding mechanism
8 drying mechanism
9 first pumping mechanism
10 second pumping mechanism
11 mounting holes
31 support frame
32 supporting arm
33 clamping head
34 container
41 motor
42 support table
61 moving block
62 stand
63 rod
71 hopper
72 dispenser
73 feeding mechanism hanger
81 fan
82 collecting cylinder
83 drying mechanism hanger
84 blowing port

What is claimed is:

1. A pretreatment device for food safety detection, comprising:
   a base;
   a vortex oscillator disposed on the base; and
   a container holding mechanism disposed on the base and configured to hold a container such that the container is positioned above the vortex oscillator,
   wherein the vortex oscillator is configured to cooperate with the container holding mechanism to treat materials contained in the container;
   wherein the pretreatment device further comprises a mobile apparatus and a feeding mechanism, a drying mechanism, a first pumping mechanism and a second pumping mechanism that are disposed on the mobile apparatus, wherein the feeding mechanism, the drying mechanism, the first pumping mechanism and the second pumping mechanism are capable of moving to and above the container under driving of the mobile apparatus,
   wherein the first pumping mechanism is configured to pump a first solvent into the container;
   wherein the feeding mechanism is configured to supply an extraction salt into the container;
   wherein the drying mechanism is configured to dry a liquid in the container; and
   wherein the second pumping mechanism is configured to pump a second solvent into the container.

2. The pretreatment device according to claim 1, wherein at least one of the first pumping mechanism and the second pumping mechanism is provided with a platen, which is configured to press against a top of the container to initiate a vortex oscillation of the container.

3. The pretreatment device according to claim 1, wherein the container holding mechanism comprises a support frame, a supporting arm extending from the support frame and a clamping head disposed on an end of the supporting arm away from the support frame, and wherein the clamping head is configured to clamp the container.

4. The pretreatment device according to claim 1, wherein the mobile apparatus comprises a translation mechanism, a slewing mechanism and/or a lifting mechanism.

5. The pretreatment device according to claim 4, wherein the lifting mechanism comprises a moving block, a stand and a rod, the rod extends in a vertical direction and is fixed to the stand, the moving block is configured to be movable on the rod, and the feeding mechanism, the drying mechanism, the first pumping mechanism and/or the second pumping mechanism is/are fixedly mounted to the moving block.

6. The pretreatment device according to claim 5, wherein the moving block is configured to have a hexahedral profile, wherein the feeding mechanism, the first pumping mechanism and the second pumping mechanism are respectively fixed to three surfaces of the moving block parallel to an extending direction of the rod, and the drying mechanism is fixed to the stand.

7. The pretreatment device according to claim 1, wherein the feeding mechanism comprises a hopper, a dispenser and a feeding mechanism hanger, wherein the hopper is configured for containing the extraction salt, the dispenser is arranged at an outlet of the hopper for dispensing the extraction salt.

8. The pretreatment device according to claim 1, wherein the drying mechanism comprises a fan, an air collecting cylinder, a blowing port, and a drying mechanism hanger.

9. A pretreatment method for food safety detection, using the pretreatment device for food safety detection according to claim 1.

10. A pretreatment method for food safety detection, using the pretreatment device for food safety detection according to claim 2.

11. A pretreatment method for food safety detection, using the pretreatment device for food safety detection according to claim 3.

12. A pretreatment method for food safety detection, using the pretreatment device for food safety detection according to claim 4.

13. A pretreatment method for food safety detection, using the pretreatment device for food safety detection according to claim 5.

14. A pretreatment method for food safety detection, using the pretreatment device for food safety detection according to claim 6.

15. A pretreatment method for food safety detection, using the pretreatment device for food safety detection according to claim 7.

16. A pretreatment method for food safety detection, using the pretreatment device for food safety detection according to claim 8.

\* \* \* \* \*